United States Patent [19]

Chiarino et al.

[11] Patent Number: 4,638,003
[45] Date of Patent: Jan. 20, 1987

[54] 1-(4-ALKYLTHIOPHENYL)-2-(SUB-STITUTED OR UNSUBSTITUTED PIPERAZINE-1-YL)-1,3-PROPANEDIOL, PHARMACEUTICAL COMPOSITIONS CONTAINING THEM USEFUL AS ANTIARRHYTHMIC AND VASODILATING AGENTS

[75] Inventors: Dario Chiarino, Monza; Angelo Carenzi, Busto Arsizio; Davide Della Bella, Milan; Mario Fantucci, Piazza Brembana, all of Italy

[73] Assignee: Zambon S.p.A., Vincenza, Italy

[21] Appl. No.: 636,714

[22] Filed: Aug. 1, 1984

[30] Foreign Application Priority Data

Aug. 5, 1983 [IT] Italy ................. 22451 A/83

[51] Int. Cl.$^4$ ................. A61K 31/495; A61K 31/135; C07D 241/04
[52] U.S. Cl. ................. 514/255; 514/648; 514/649; 514/653; 544/396; 544/398; 544/401; 544/402; 564/316; 564/360
[58] Field of Search ............... 544/402, 396, 398, 401; 514/255, 648, 649, 653; 564/360, 316

[56] References Cited

U.S. PATENT DOCUMENTS 2,759,970  8/1956  Suter ................. 260/562
3,056,799  10/1962  Tullar ................. 260/319
3,954,871  5/1976  Roba ................. 260/501.17
4,226,808  10/1980  Nagabhushan ................. 564/212

FOREIGN PATENT DOCUMENTS 149750  8/1973  Czechoslovakia .
 66919  12/1982  European Pat. Off. .
49-87638  8/1974  Japan .

OTHER PUBLICATIONS

Nagabhushan, Chem. Abst. 94:46988x (1981) eg. U.S. Pat. No. 4,226,808.
Diana et al., Chem. Abst. 70:11252e (1969).
Budai et al., Chem. Abst. 77:5165g (1972).
Kvita et al., Chem. Abst. 80:59684f (1974) eg. Czech 149750.
Budai et al., Chem. Abst. 77:88069c (1972).
Bejamin F. Tullar, Chem. Abst. 58:576d eg. U.S. Pat. No. 3,056,799.
Portelli et al., Chem. Abst. 97:5886f (1982).

Primary Examiner—Donald G. Daus
Assistant Examiner—Cecilia Shen
Attorney, Agent, or Firm—Cushman, Darby & Cushman

[57] ABSTRACT

N-substituted derivatives of 1-(4'-alkylthiophenyl)-2-amino-1,3-propanediol, their salts with pharmaceutically acceptable organic and inorganic acids, processes for preparing them, pharmaceutical compositions containing them and intermediates useful in the preparation thereof.

The novel derivatives according to this invention are endowed with calcium antagonist activity and are useful as antiarrhythmic and vasodilating agents.

17 Claims, No Drawings

1-(4-ALKYLTHIOPHENYL)-2-(SUBSTITUTED OR UNSUBSTITUTED PIPERAZINE-1-YL)-1,3-PROPANEDIOL, PHARMACEUTICAL COMPOSITIONS CONTAINING THEM USEFUL AS ANTIARRHYTHMIC AND VASODILATING AGENTS

DESCRIPTION

This invention relates to novel N-substituted derivatives of 1-(4'-alkylthiophenyl)-2-amino-1,3-propanediol, to their salts with pharmaceutically acceptable organic and inorganic acids, to the processes for preparing them, to the pharmaceutical compositions containing them and to intermediates useful in the preparation thereof.

More particularly this invention relates to the compounds of Formula:

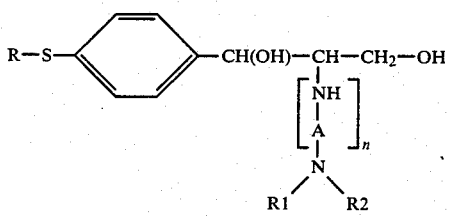

wherein
R is an alkyl radical having from 1 to 4 carbon atoms;
n is 0 or 1;
A is an alkyl radical having from 2 to 6 carbon atoms;
R1 is hydrogen or an alkyl radical having from 1 to 6 carbon atoms;
R2 is an alkyl radical having from 1 to 6 carbon atoms, a phenoxyalkyl radical, a mono- or di-phenylalkyl radical where the alkyl radical has from 1 to 6 carbon atoms and the phenyl moiety can be substituted by one or two substituents, equal or different between them, which are selected from the group comprising halogen, 1–4 C alkyl and 1–4 C alkoxy, or
R1 and R2, together with the nitrogen atom to which they are linked, form a 5–6 membered heterocyclic ring which can contain another hetero-atom selected from the group comprising oxygen, sulfur, nitrogen and nitrogen substituted by a 3–6 C cycloalkyl, a 1–6 C alkyl or by a mono- or a diphenylalkyl radical where, in turn, the alkyl radical has from 1 to 6 carbon atoms and the phenyl moiety can be substituted by one or two substituents, equal or different between them, which are selected from the group comprising halogen, 1–4 C alkyl and 1–4 C alkoxy,
and their salts with pharmaceutically acceptable organic or inorganic acids.

The compounds (I) can exist in various stereoisomeric forms in that they contain two asymmetric carbon atoms and other asymmetric carbon atoms may present in R1 and R2. This invention relates either each stereoisomer or the mixtures thereof.

As to the meanings of A, R, R1 and R2, the term "alkyl" is intended to comprise either straight or branched chains as well as saturated and unsaturated chains.

Preferred meanings are:
R=methyl or ethyl;
n=0 or 1;
A=ethyl;
R1=hydrogen, methyl or ethyl;
R2=alkyl radical having from 1 to 4 carbon atoms, phenoxyalkyl radical, mono- and diphenylalkyl radical where the alkyl radical has from 1 to 6 C atoms and the phenyl moiety can be substituted by one or two substituents, equal or different between them, which are selected from the group comprising halogen and 1–4 C alkoxy,
R1 and R2, together with the nitrogen atom to which they are linked, form a piperazinyl radical where the terminal nitrogen is substituted by a cyclohexyl, a diphenylmethyl or a di(fluorophenyl)methyl radical.

The compounds (I) according to this invention can be prepared according to various methods.

The preferred method is consisting in reacting a propanediol of Formula I wherein n is 0 and R1=R2=H, with a suitable carbonyl derivative to afford an acylamino derivative or a Schiff base and in their subsequent reduction to give the compounds I wherein R1=H.

Some intermediates which are thus obtained are novel and are a further object of this invention.

More particularly, are novel the compounds of Formula

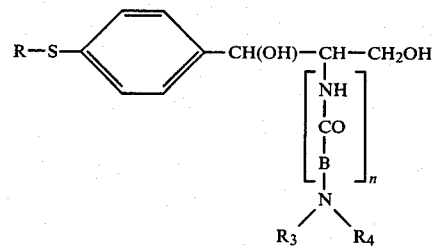

wherein
R is an alkyl radical having from 1 to 4 carbon atoms;
B is an alkyl radical having from 1 to 5 carbon atoms, and
when n is 0
R3 is hydrogen,
R4 is a phenyloxyalkanoyl, a mono or a di-diphenylalkanoyl radical, where the alkanoyl radical has from 1 to 6 carbon atoms and the phenyl moiety can be substituted by one or two substituents, equal or different between them, which are selected from the group comprising halogen, 1–4 C alkyl and 1–4 C alkoxy, or
R3 and R4, together, are phenoxyalkylidine, mono- or di-phenylalkylidene, where the alkylidene radical has from 1 to 6 carbon atoms and the phenyl moiety can be substituted by one or two substituents, equal or different between them, which are selected from the group comprising halogen, 1–4 C alkyl or 1–4 C alkoxy,
and when n is 1,
R3 is an alkyl having from 1 to 6 carbon atoms,
R4 is an alkyl having from 1 to 6 carbon atoms, or
R3 and R4, together with the nitrogen atom to which they are linked, form a 5–6 membered heterocyclic ring which can contain another hetero-atom selected from the group comprising oxygen, sulfur, nitrogen and nitrogen substituted by a 3-6 C cycloalkyl, a 1-6 C alkyl or by a mono- or a diphenylalkyl radical where, in turn, the alkyl radical has from 1 to 6 carbon atoms and the phenyl moiety can be substituted by one or two substituents, equal or different between them, which are selected from the group comprising halogen, 1-4 C alkyl and 1-4 C alkoxy.

Suitable carbonyl derivatives which can be reacted with the compounds of Formula I where R1=R2=H are the aldehydes, the ketones or the acyl halides, esters and anhydrides.

When the carbonyl derivative is an acyl halide, the reaction is preferably carried out according to known techniques in the presence of a suitable diluent and of an organic or inorganic base to capture the hydrogen halide formed during the reaction.

When the carbonyl derivative is an aldehyde or a ketone the reaction is preferably carried out according to known techniques by using an apparatus which allows to separate the water formed during the reaction. An example of such an apparatus is the Dean and Stark separator.

Also the subsequent reduction of the acylamino derivative or of the Schiff base is carried out according to known techniques. In case of acylamino derivatives the preferred reducing agent is lithium aluminium hydride.

In case of Schiff bases the preferred reducing agents are lithium aluminium hydride and sodium borohydride.

The thus obtained compound of Formula I where R is hydrogen can be, if desired, again alkylated. Also this reaction is carried out according to known techniques such as the Leuckart-Wallach reaction.

Another method particularly useful for preparing the compounds of Formula I where R1 and R2 form a heterocyclic ring is consisting in reacting a compound of Formula I wherein both R1 and R2 are hydrogen with a suitable compound of formula $X-(CH_2)_n-Y-(CH_2)_m-X$ wherein n is 1, 2 or 3, m is 1, 2 or 3, provided that m+n is 3 or 4, X is halogen, mesyloxy or tosyloxy, Y is O, S, NH or a tertiary nitrogen. Also this reaction is carried out by capturing the hydrogen halide which is formed according to known techniques such as, for example, the addition of suitable organic or inorganic bases.

Alternatively, the above mentioned techniques can be applied to a precursor which can then be easily transformed into the desired compound of Formula I.

Examples of useful precursors are the aminoketones of Formula

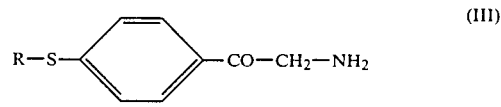

wherein R has the above mentioned meanings, which can firstly be acylated and then treated with formaldehyde to give a 1-(p-alkylthiophenyl)-2-acylamino-1,3-propanediol which is finally reduced to the corresponding compound of Formula I.

The reduction of the keto group to alcohol and that of the acylamino group or of the Schiff base can proceed contemporaneously or in the desired sequence.

In view of the desired final compound as well as of the cost and of the availability of the raw materials, the artisan will be able to choose case by case other strategies of synthesis which make use of known techniques.

The novel Compounds of Formula I are endowed with calcium antagonist activity and are useful as antiarrhythmic and vasodilating agents.

The evaluation of the calcium antagonist activity has been performed on isolated rabbit aorta according to the test of A. Brockaert and T. Godfraind (Eur. J. Pharmacol. 53, 281-288, 1979).

The antagonist effect has been referred as ratio between the $CaCl_2$ concentration producing a 50% contraction of the vascular smooth muscle in presence or in absence (Table 2) of various compounds ($10^{-6}$M, $10^{-5}$M).

The relationship between the chemical structure of various compounds and their code numbers is shown in Table 1.

The evaluation of the antiarrhythmic activity has been performed in the anesthetized rat with the method of M. Malinov et al. (Am. J. Physiol. 172, 743-746, 1953).

Arrythmia has been induced by administering (0.25 ml in 30 seconds) a saline solution containing 15% of calcium chloride into the jugular vein.

TABLE 1

RELATIONSHIP BETWEEN CHEMICAL STRUCTURE AND CODE NUMBER

| CODE NUMBER | R | $R_1$ | n | $R_2$ | CONFIGURATION | SALT |
|---|---|---|---|---|---|---|
| Z 1382 | $CH_3$ | H | 0 | $-CH_2-CH_2-CH(C_6H_5)_2$ | 1S, 2S | acid maleate |
| Z 1373 | $CH_3$ | H | 0 | " | 1R, 2S | " |
| Z 1468 | $CH_3$ | $CH_3$ | 0 | " | 1S, 2S | — |
| Z 1477 | $CH_3$ | H | 0 | $-CH_2-CH_2-CH-(4\text{-fluorophenyl})_2$ | 1S, 2S | hydrochloride |
| Z 1490 | $CH_3$ | $CH_3$ | 0 | " | 1S, 2S | 4-hydroxybenzoate |
| Z 1415 | $CH_3$ | H | 0 | $-CH_2-CH(C_6H_5)_2$ | 1S, 2S | hydrochloride |
| Z 1416 | $CH_3$ | H | 0 | $-CH(C_6H_5)_2$ | 1S, 2S | hydrochloride |
| Z 1410 | $CH_3$ | H | 0 | $-CH(CH_3)-CH_2-C_6H_5$ | 1S, 2S, 1'RS | hydrochloride |
| Z 1411 | $CH_3$ | H | 0 | $-CH(CH_3)-CH_2-CH_2-C_6H_5$ | 1S, 2S, 1'S* | hydrochloride |
| Z 1431 | $CH_3$ | H | 0 | " | 1R, 2R, 1'R | hydrochloride |
| Z 1428 | $CH_3$ | $CH_3$ | 0 | " | 1S, 2S, 1'S* | hydrochloride |
| Z 1409 | $CH_3$ | H | 0 | $-CH_2-CH(CH_3)-C_6H_5$ | 1S, 2S, 2'RS | hydrochloride |
| Z 1413 | $CH_3$ | H | 0 | $-CH(CH_3)-C_6H_5$ | 1S, 2S, 1'S* | — |
| Z 1414 | $CH_3$ | H | 0 | " | 1S, 2S, 1'R* | — |
| Z 1393 | $CH_3$ | H | 0 | $-CH(CH_3)-CH_2-O-C_6H_5$ | 1S, 2S, 1'S* | hydrochloride |
| Z 1457 | $CH_3$ | $CH_3$ | 0 | $-CH(CH_3)-CH_2-O-C_6H_5$ | 1S, 2S, 1'S* | — |
| Z 1394 | $CH_3$ | H | 0 | " | 1S, 2S, 1'R* | glycolate |
| Z 1407 | $CH_3$ | H | 0 | " | 1R, 2R, 1'R* | hydrochloride |
| Z 1408 | $CH_3$ | H | 0 | " | 1R, 2R, 1'S* | glycolate |
| Z 1429 | $CH_3$ | H | 0 | $-CH(CH_3)-CH_2-3,4$-dimethoxyphenyl | 1S, 2S, 1'S* | hydrochloride |
| Z 1440 | $CH_3$ | H | 0 | " | 1R, 2R, 1'R* | hydrochloride |
| Z 1434 | $CH_3$ | H | 0 | $-CH(CH_3)-CH_2-CH_2-3,4$-dimethoxyphenyl | 1S, 2S, 1'S* | hydrochloride |

TABLE 1-continued
RELATIONSHIP BETWEEN CHEMICAL STRUCTURE AND CODE NUMBER

| CODE NUMBER | R | $R_1$ | n | $R_2$ | CONFIGURATION | SALT |
|---|---|---|---|---|---|---|
| Z 1489 | $CH_3$ | $CH_3$ | 0 | " | 1S, 2S, 1'S* | — |
| Z 1466 | $CH_3$ | | 0 | $= R_1 + R_2 =$ ⬡N—$CH_2$—$C_6H_5$ | 1S, 2S | dihydrochloride |
| Z 1491 | $CH_3$ | = | 1 | $R_1 + R_2 =$ ⬡N—$CH(4\text{-fluorophenyl})_2$ | $A = C_2H_4$ | sulfate |
| Z 1418 | $CH_3$ | $C_2H_5$ | 1 | $A = C_2H_4$  $R_2 = C_2H_5$ | 1S, 2S | acid dimaleate |
| Z 1412 | $CH_3$ | | 0 | $= R_1 + R_2 =$ ⬡N—H⬡ | 1S, 2S | dihydrochloride |
| Z 1439 | $CH_3$ | N | 0 | $= R_1 + R_2 =$ ⬡N—$CH(C_6H_5)_2$ | 1S, 2S | dihydrochloride |

The asterisk has been used to distinguish one diastereoisomer from the other as follows:
R, R, R* and S, S, S* are used in connection with the diasteroisomer having the highest retention time in TLC (eluent: dichloromethane/methyl alcohol/ammonium hydroxide).

TABLE 2
Isolated rabbit aorta: ratio between the $CaCl_2$ concentration producing the 50% contraction in presence or in absence of various compounds (10, 10 M).

| COMPOUND | CONCENTRATION IN PERFUSED LIQUID | |
|---|---|---|
| | $10 M^{-6}$ | $10^{-5} M$ |
| Z. 1382 | 20 | 255 |
| Z. 1373 | 9 | 86 |
| Z. 1431 | 5 | 47 |
| Z. 1434 | 5 | 21 |
| Z. 1415 | 6 | 27 |
| Z. 1428 | 2 | 30 |
| Z. 1439 | 4 | 24 |
| Z. 1409 | 4 | 12 |
| Z. 1411 | 10 | 15 |
| Z. 1394 | 3 | 7 |
| Prenylamine | 12 | 62 |
| Cinnarizine | 1 | 22 |
| Flunarizine | 1 | 16 |

TABLE 3
Antiarrythmic activity (induced by calcium chloride) after intravenous administration in anesthetized rat.

| COMPOUND | DOSE $\mu$mols/Kg/i.v. | NUMBER OF PROTECTED RATS/ TOTAL NUMBER | $ED_{50}$ $\mu$mols/kg |
|---|---|---|---|
| Z. 1382 | 7.6 | 1/8 | 19 |
| | 13.4 | 4/8 | |
| | 20 | 3/8 | |
| | 27 | 5/8 | |
| Z. 1409 | 8 | 0/8 | 43 |
| | 16 | 2/8 | |
| | 24 | 3/8 | |
| | 48 | 5/8 | |
| Z. 1411 | 8 | 0/8 | 13 |
| | 12 | 4/8 | |
| | 16 | 6/8 | |
| Z. 1408 | 16 | 1/8 | 35 |
| | 32 | 4/8 | |
| | 56 | 6/8 | |
| Verapamil | 4.4 | 2/8 | 6 |
| | 7.7 | 5/8 | |
| | 11 | 6/8 | |

TABLE 4
Coronary dilating activity after intravenous administration in anesthetized rat. Tolerability and therapeutic index.

| | Coronary dilating activity | Tolerability | |
|---|---|---|---|
| COMPOUND | $ED_{50}$ nmols/kg/i.v. | Heart rate ($-20\%$) nmols/kg | Therapeutic index |
| Z. 1434 | 0.45 | 42 | 93 |
| Z. 1382 | 0.84 | 17 | 20 |
| Z. 1409 | 0.84 | 73 | 87 |
| Z. 1411 | 1.0 | 44 | 44 |
| Z. 1431 | 2.6 | 76 | 29 |
| Z. 1415 | 2.9 | 49 | 17 |
| Z. 1439 | 3.3 | 23 | 7 |
| Z. 1373 | 3.4 | 23 | 7 |
| Z. 1393 | 3.8 | 35 | 9 |
| Z. 1407 | 3.2 | 53 | 17 |
| Z. 1408 | 3.7 | 76 | 21 |
| Z. 1414 | 4.0 | 100 | 25 |
| Z. 1413 | 4.5 | 230 | 51 |
| Verapamil | 0.15 | 4.1 | 27 |
| Flunarizine | 0.48 | — | — |
| Cinnarizine | 0.86 | — | — |
| Nifedipine | 0.57 | — | — |
| Prenylamine | 1.84 | 19 | 11 |

In these experimental conditions arrythmia occurs in the 90% of the animals. The compounds have been administered intravenously ten minutes before calcium chloride. The antiarrythmic activity has been referred as dose effective to antagonize the appearance of arrythmia in the 50% of the treated animals ($ED_{50}$).

The result are shown in Table 3.

The evaluation of the coronary dilating activity has been performed with the method of O. Nieschultz, et al. (Arzneim. Forsch. 5, 680, 1955). The coronary spasm induced by Vasopressin corresponds to the flattering of T wave in the E.C.G. The coronary dilating activity of the compounds has been referred as dose effective 50 in restoring the T wave in the 50% of the animals within 2 minutes after the administration. The compounds have been administered intravenously 60 seconds after Vasopressin.

The results are shown in Table 4.

Furthermore, tolerability has been tested in the same experimental conditions in which it has been performed the pharmacological study in vivo.

The tolerability test has been carried out by solubilizing the compounds in 40% glyceril formal.

Tolerability has been referred as effective dose to reduce heart rate of 20%. Therapeutic index has been determined as ratio between the dose inducing bradycardia 20 and the effective anti-anginal dose 50.

The results are shown in Table 4.

The experimental data prove that the compounds of this invention show a remarkable calcium antagonist activity even when compared with known drugs.

In addition, their calcium antagonist activity is very specific because the same compounds are not active when tested on the rabbit aorta contraction induced by norepinephrine (Eur. J. Pharmacol. 53, 281–283, 1975) at those concentrations which had been previously used to test the antagonism induced by calcium chloride.

Finally, a further object of this invention are the pharmaceutical compositions containing, as active ingredient, the compounds of Formula I or their pharmaceutically acceptable salts together with organic or inorganic solid or liquid, pharmaceutical excipients.

The pharmaceutical dosage forms can be solid, such as tablets, dragées, capsules, powders, granules and suppositories, or liquid such as solutions, suspensions and emulsions, or semi-solids such as creams and ointments.

They can be also prepared in such a way to allow a substained release of the drug.

In addition they may contain preserving agents, stabilizers, wetting or emulsifying agents, salts for regulating the osmotic pressure, buffers, dyestuffs, flavouring agents etc.

They may be prepared according to known methods and may further contain other therapeutic ingredients.

The following examples are given to illustrate this invention, without limiting it in any way.

EXAMPLE 1

(a) (1R,2R)-1-(4-methylthiophenyl)-2-amino-1,3-propanediol (20 g; 98 mmols) is dissolved into a mixture of 1000 ml ethyl acetate and 600 ml of 0.5N of potassium hydroxide under stirring at 5° C.

To the thus obtained solution are added in 1 hour and contemporaneously a solution of 3,3-diphenylpropionyl chloride (24 g; 98 mmols) in 220 ml of ethyl ether and 220 ml of 0.5N potassium hydroxide, while maintaining the pH at 7–8.

When the addition is over, precipitates a crystalline solid which, after 15 minutes at room temperature and under stirring, is collected by filtration (29.2 g).

The filtrate is washed twice with 0.5M sulfuric acid, then with 5% sodium bicarbonate aqueous solution and finally with water.

The organic extracts are dried over sodium sulfate and evaporated to dryness; 13 g.

The filtrate and the residue of the evaporation are combined and purified by dissolution in hot ethyl alcohol (450 ml), the solution is decoulored with active carbon and filtered; the filtrate is treated with water (380 ml) under stirring. After cooling, the precipitate is collected by filtration. (1R,2R)-1-(4-methylthiophenyl)-2-(3,3-diphenylpropionylamino)-1,3-propanediol is thus obtained, 37.20 g; Yield, 90%; m.p. 168°–170° C.

In analogous manner has been prepared the enantiomer having 1S,2S configuration.

(b) A solution of (1S,2S)-1-(4-methylthiophenyl)-2-(3,3-diphenylpropionylamino)-1,3-propanediol (15 g; 35.5 mmols) in anhydrous tetrahydrofuran (180 ml) is dropped into a suspension of lithium aluminium (8 g; 210 mmols) in anhydrous tetrahydrofuran (360 ml) kept under vigorous stirring.

The thus obtained mixture is refluxed under stirring for about 45 hrs.

After cooling to 5° C., a 1:1 mixture (50 ml) of water and tetrahydrofuran is added under vigorous stirring.

The mixture is filtered through "theorite nr. 5" and the filtrate is evaporated to dryness.

The residue is extracted with ethyl ether and the extracts are washed with water and evaporated to dryness.

The oily residue (14.5 g) is dissolved in ethyl alcohol (70 ml). To the thus obtained solution is added maleic acid (4.5 g; 38.8 mmols) in ethyl alcohol (41 ml).

After cooling the precipitate (12.5 g) is filtered and purified by crystallization from water.

(1S,2S)-1-(4-methylthiophenyl)-2-(3,3-diphenylpropylamino)-1,3-propanediol acid maleate; 8.4 g; Yield, 45%; m.p. 168°–170° C.

Analogously has been prepared the enantiomer having configuration (1R,2R).

EXAMPLE 2

A mixture of (1S,2S)-1-(4-methylthiophenyl)-2-amino-1,3propanediol (42.6 g; 0.2 mol), acetophenone (37.5 ml; 0.32 mol) and of concentrate sulfuric acid (0.5 ml) is heated for 1 hour at 150° C. Meantime some water is formed.

Toluene (50 ml) is added and the mixture is refluxed for two hours with a Dean and Stark apparatus.

About 3 ml of water are separated and collected.

The reaction mixture is then diluted with chloroform, filtered and evaporated until is obtained an oily residue. This oil is dissolved in anhydrous tetrahydrofuran (250 ml) and dropped into a suspension of lithium aluminium hydride (27.2 g) in tetrahydrofuran (1 l).

After two hours the hydride in excess is destroyed and the reaction mixture is filtered through "theorite nr. 5". The solvent is evaported. The residue is dissolved in dichloromethane and the solution is washed to neutral with water, dried and evaporated under reduced pressure to afford an oil.

The thus obtained base is a mixture of diasteroisomers which have been separated by chromatography through a silica gel column; eluent, dichloromethane/methyl alcohol 92.5/7.5.

The product having the lower retention volume is dissolved in ethyl acetate and this solution is made acid with ethereal hydrochloric acid up to pH 1. After cooling crystallizes the (1S,2S,1′S*)-1-(4-methylthiophenyl)-2-(1-methylbenzylamino)-1,3-propanediol hydrochloride; m.p. 163°–165° C. (ethyl acetate).

The product having the higher retention volume is the isomer 1S,2S,1'R*; m.p. 94°–95° C. (isopropyl ether).

EXAMPLE 3

Borotrifluoride etherate (3.5 ml) is added to a mixture of (1S,2S)-1-(4-methylthiophenyl)-2-amino-1,3-propanediol (42.6 g; 0.2 mol), benzophenone (36.4 g; 0.2 mol) and anhydrous xylene (300 ml) and the thus obtained suspension is refluxed for 3 hours.

Benzene (50 ml) is added, an apparatus of Dean and Stark is filled and the mixture is refluxed for further two hours. About 3 ml of water are collected.

The reaction mixture is filtered through "Theorite nr. 5" and evaporated under reduced pressure to afford an oily residue (66.4 g).

This oil is dissolved in anhydrous tetrahydrofuran (250 ml) and the thus obtained solution is slowly dropped into a suspension of lithium aluminium hydride (20 g; 0.528 mol) in tetrahydrofuran (1 l) while the temperature is maintained below 30° C.

The stirring is continued for 3 hours at room temperature and for further 3 hours at 50° C.

The reaction mixture is cooled to +5° C. and treated carefully with 50% aqueous tetrahydrofuran (250 ml).

After filtration through "theorite nr. 5" and evaporation of the solvent, to the residue are added dichloromethane and water and the organic phase is washed till neutral, dried and evaporated under reduced pressure.

The crystalline residue is crystallized twice from acetonitrile.

(1S,2S)-1-(4-methylthiophenyl)-2-diphenylmethylamino-1,3-propanediol is obtained (36 g), m.p. 132°–134° C.

The base is dissolved in hot ethyl acetate and added with ethereal hydrochloric acid up to pH 1.

After cooling crystallizes the hydrochloride salt, m.p. 194°–198° C. (water).

EXAMPLE 4

A suspension of (1S,2S)-1-(4-methylthiophenyl)-2-amino-1,3-propanediol (27.45 g; 0.129 mol) in anhydrous chloroform (200 ml) and 3,4-dimethoxyphenylacetone (25 g; 0.129 mol), containing 0.3 ml of concentrate sulfuric acid, is refluxed for six hours and the water which is formed (about 2.5 ml) is separated.

The warm solution is filtered, concentrated in vacuo until is obtained a solid residue (64.5 g), containing mainly the Schiff base.

The base is dissolved in anhydrous methyl alcohol (1,3 l), to this solution is added slowly sodium borohydride (24.8 g; 0.655 mol) at room temperaure. When the addition is complete the stirring is continued for 1 hour and then the reaction mixture is cooled to +10° C. and made acid with conc. hydrochloric acid up to pH 1.

After evaporation of the alcohol under reduced pressure, the residue is dissolved in water, the suspension is alkalinized with potassium carbonate and extracted many times with dichloromethane.

The combined extracts are dried and evaporated under reduced pressure until is obtained a yellow residue.

The rough base is dissolved in ethyl alcohol and treated with ethereal hydrochloric acid up to pH 1.

After cooling crystallizes one of the stereoisomers of (1S,2S) -1-(4-methylthiophenyl)-2-[1-methyl-2-(3,4-dimethoxyphenyl)ethylamino]-1,3-propanediol hydrochloride (33.6 g) m.p. 182°–184° C. (ethyl alcohol).

Analogously, has been prepared the form (1R,2R) and the compound: (1S,2S)-1-(4-methylthiophenyl)-2-[1-methyl-3-(3,4-dimethoxyphenyl)-propylamino]-1,3propanediol hydrochloride m.p. 158°–160° C. (isopropanol).

EXAMPLE 5

A suspension of (1S,2S)-1-(4-methylthiophenyl)-2-amino-1,3-propanediol (42.6 g; 0.2 mol) in chloroform (200 ml) and 2-phenylpropionaldehyde (28 ml; 0.209 mol) is refluxed for 3 hours and a half and the water which is formed (about 4 ml) is separated.

The solution is filtered and the solvent is evaporated until an oily residue is obtained.

The residue is dissolved in anhydrous tetrahydrofuran (250 ml) and dropped into a suspension of lithium aluminium hydride (22.7 g; 0.6 mol) in tetrahydrofuran (1 l) while the temperature is kept below 30° C.

After two hours the reaction mixture is treated carefully with 50% aqueous tetrahydrofuran (250 ml), filtered through "Theorite nr. 5" and evaporated under reduced pressure.

The residue is dissoved in ethyl ether and the solution is washed to neutral with water, dried and evaporated under reduced pressure.

The thus obtained oily residue (64.7 g) is dissolved in ethyl alcohol and made acid with ethereal hydrochloric acid up to pH 1.

The precipitate is collected by filtration and crystallized twice from acetonitrile. Are thus obtained 28.3 g of (1S,2S)-1-(4-methylthiophenyl)-2-(2-phenylpropylamino)-1,3-propanediol hydrochloride, m.p. 173°–175° C. (acetonitrile).

In analogous manner has been prepared: (1S,2S)-1-(4-methylthiophenyl)-2-(2,2-diphenylethylamino)-1,3-propanediol, m.p. 160°–162° C. (acetonitrile.

EXAMPLE 6

A suspension of (1S,2S)-1-(4-methylthiophenyl-2-amino-1,3-propanediol (42.6 g; 0.2 mol), benzylacetone (30 ml; 0.21 mol), anhydrous chloroform (200 ml) and of conc. sulfuric acid (0.3 ml) is refluxed in an apparatus suitable for collecting water for 4 hours until about 4 ml of water are collected.

The solution is filtered and evaporated until an oily residue is obtained.

This oil is dissolved in anhydrous tetrahydrofuran (250 ml) and dropped into a suspension of lithium aluminium hydride (22.5 g) in tetrahydrofuran while the temperature is maintained between 25° C. and 30° C.

When the addition is complete, the stirring is continued for two hours; the hydride in excess is then destroyed.

After filtration and evaporation of the solvent, the residue is treated with dichloromethane and the solution is washed with water till neutral.

The organic layer is dryed with sodium sulfate and evaporated to dryness.

The oily residue is treated with ethereal hydrochloric acid in ethyl alcohol.

(1S,2S)-1-(4-methylthiophenyl)-2-(1-methyl-3-phenylpropylamino)-1,3-propanediol hydrochloride (24 g) is thus obtained and is then recrystallized from acetonitrile (300 ml) and ethyl alcohol (10 ml).

Yield, 21.5 g of a pure diasteroisomer which melts at 163°–165° C.

In analogous manner has been prepared the enantiomer (1R,2R) and the compound: (1S,2S)-1-(4-methylthiophenyl)-2-(1-methyl-2-phenylethylamino)-1,3-propanediol hydrochloride, m.p. 213°–215° C. (water).

EXAMPLE 7

(1S,2S)-1-(4-methylthiophenyl)-2-(1-methyl-3-phenylpropylamino)-1,3-propanediol (9.9 g; 28.6 mmols) is added under stirring to 90% formic acid (10 g).

To this solution is added 40% formaldehyde (3.22 ml).

After heating at 100° C. for 8 hours, the solution is cooled to room temperature and 4N hydrochloric acid (13.5 ml) is added. The solid which precipitates is collected and added with dichloromethane and 5% sodium hydroxyde. The organic layer is washed, dried and evaporated under reduced pressure. The oily residue (7.7 g) is dissolved in ethyl alcohol and converted into the corresponding hydrochloride.

By crystallization from ethyl alcohol are thus obtained 6.6 g of (1S,2S)-1-(4-methylthiophenyl)-2-methyl-(1-methyl-2-phenylethyl)-amino-1,3propanediol hydrochloride, m.p. 190°–192° C.

EXAMPLE 8

A mixture of (1S,2S)-1-(4-methylthiophenyl)-2-amino-1,3-propanediol (10.6 g; 50 mmols), N,N-bis-(beta-chloroethyl)-cyclohexylamine hydrochloride (14 g; 53.7 mmols), sodium bicarbonate (17 g; 200 mmols) and of anhydrous ethyl alcohol (80 ml) is refluxed for 3,5 hours and the solvent is then evaporated; chloroform and water and added to the thus obtained residue.

The organic layer is washed with water, dried and evaporated under reduced pressure.

The thus obtained amorphous residue (21.6 g) is crystallized from 1,2-dichloroethane (180 ml).

(1S,2S)-1-(4-methylthiophenyl)-2-(4-cyclohexylpiperazin-1-yl)-1,3-propanediol (7.9 g) is obtained.

The corresponding hydrochloride melts at 235°–237° C. (dec.) (ethyl alcohol).

In analogous manner has been prepared the (1S,2S)-1-(4-methylthiophenyl)-2-(4-diphenylmethylpiperazin-1-yl)-1,3-propanediol dihydrochloride, m.p. 185°–187° C. (dec.) (methyl alcohol and water).

The following Compounds of Formula I have been prepared according to methods similar to those disclosed in the above Examples:

R=CH₃; R1=H; R2=—CH(CH₃)—CH₂—O—C₆H₅; n=0 configuaration: 1S,2S,1'S*; salt: hydrochloride; m.p. 150°–152° C.

R=CH₃, R1=H; R2=—CH(CH₃)—CH₂—O—C₆H₅; n=0 configuration: 1S,2S,1'R*, salt: glycolate; m.p. 118°–120° C. R=CH₃, R1=H, R2=—CH(CH₃)—CH₂—O—C₆H₅; n=0 configuration: 1R,2R,1'R*; salt: hydrochloride, m.p. 151°–153° C.

R=CH₃; R1=H, R2=—CH(CH₃)—CH₂—O—C₆H₅; n=0 configuration: 1R,2R,1'S*; salt: glycolate; m.p. 118°–120° C.

R=CH₃, R1=CH₃, R2=—CH(CH₃)—CH₂—O—C₆H₅; n=0 configuration 1S,2S,1'S*; m.p. 68°–70° C.

R=CH₃, R1=C₂H₅, R2=—C₂H₅A=C₂H₄; n=1 configuration: 1S,2S; salt: acid dimaleate, m.p. 108°–110° C.

R=CH₃, R1=C₂H₅, R2=—C₂H₅, B=CH₂, n=1 configuration: 1S,2S; salt; 4-hydroxybenzoate, m.p. 80°–82° C.

R=CH₃,R1=CH₃, R2=—CH₂—CH₂—CH(C₆H₅)₂; n=1 configuration: 1S,2S; m.p. 87°–89° C. (isopropyl ether)

R=CH₃, R1=H, R2=—CH₂—CH₂—CH(4F—C₆H₄)₂; n=0 configuration: 1S,2S; salt: hydrochloride; m.p. 164°–165° C. (acetonitrile)

R=CH₃, R1=CH₃, R2=—CH₂—CH₂—CH(4F—C₆H₄)₂; n=0 configuration: 1S,2S; salt: p-hydroxybenzoate; m.p. 74°–76° (dec.) (isopropyl ether)

R=CH₃, R1=CH₃, R2=—CH(CH₃)—CH₂CH₂-3,4-dimethoxyphenyl; n=0 configuration: 1S,2S,1'S*; oil

R=CH₃,R1+R2=

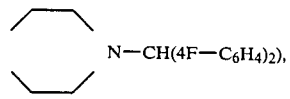

A=C₂H₄, n=1 configuration: 1S,2S; salt: sulfate; m.p. 188°–190° C. (dec.) (ethyl alcohol)

R=CH₃, R1+R2=

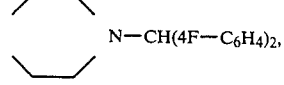

B=CH₂, n=1 configuration: 1S,2S; m.p. 136°–137° C. (isopropyl ether)

R=CH₃, R1=H, R2=—CH(4F—C₆H₄)₂, B=CH₂, n=1 configuration: 1S,2S; m.p. 109°–111° C. (dichloroethane/isopropyl ether)

R=CH₃, R1+R2=

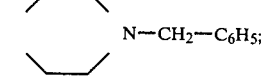

n=0 configuration: 1S,2S; salt: dihydrochloride; m.p. 219°–220° C. (methyl alcohol)

We claim:
1. A compound of the Formula

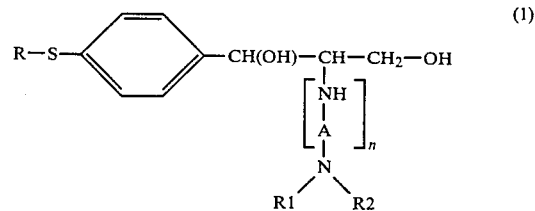

wherein
R is an alkyl having from 1 to 4 carbon atoms;
n is 0 or 1;
A is an alkyl having from 2 to 6 carbon atoms;
R1 is hydrogen or an alkyl having from 1 to 6 carbon atoms;
R2 is a phenoxyalkyl, a mono- or di-phenylalkyl where the alkyl has from 1 to 6 carbon atoms and the phenyl moiety can be substituted by one or two substituents, equal or different between them, which are selected from the group conprising halogen, 1–4 C alkyl and 1–4 C alkoxy, or R1 and R2, together with the nitrogen atom to which they are linked, form a piperozinyl ring which can be substituted on one having nitrogen by a 3-6 C cycloalkyl, a 1-6 C alkyl or by a mono- or a diphenylalkyl where, in turn, the alkyl has from 1 to 6 carbon atoms and the phenyl moiety can be substituted by one or two substituents, equal or different between them, which are selected from the group consisting halogen, 1-4 C alkyl and 1-4 C alkoxy, and pharmaceutically acceptable salts thereof with organic and inorganic pharmaceutically acceptable acids.

2. A compound according to claim 1, characterized in that

R is methyl or ethyl;
n is 0 or 1;
A is ethyl;
R1 is hydrogen, methyl or ethyl;
R2 is phenoxyalkyl, a mono- or a diphenylalkyl where the alkyl has 1-6 C and the phenyl moiety is substituted by one or two substituents, equal or different between them, which are selected from the group comprising halogen and 1-4 C alkoxy; or
R1 and R2, together with the nitrogen atom to which they are linked, form a piperazinyl where the terminal nitrogen is substituted by a cyclohexyl, a diphenylmethyl or a di(fluorophenyl)-methyl.

3. A pharmaceutical composition comprising a compound according to claim 1 in an amount suitable for use as a calcium antagonist, an antiarrhythmic agent or a vasodilating agent together with one or more pharmaceutical excipients.

4. A pharmaceutical composition comprising a compound according to claim 2 in an amount suitable for use as a calcium antagonist, an antiarrhythmic agent or a vasodilating agent together with one or more pharmaceutical excipients.

5. A method comprising administering to an animal in need thereof a calcium antagonist activity effective amount of a compound according to claim 1.

6. A method comprising administering to an animal in need thereof a calcium antagonist activity effective amount of a compound according to claim 2.

7. A method comprising administering to an animal in need thereof an antiarrhythmic effective amount of a compound according to claim 1.

8. A method comprising administering to an animal in need thereof an antiarrhythmic effective amount of a compound according to claim 2.

9. A method comprising administering to an animal in need thereof a vasodilating effective amount of a compound according to claim 1.

10. A method comprising administering to an animal in need thereof a vasodilating effective amount of a compound according to claim 2.

11. A compound according to claim 1 where n is 1.
12. a compound according to claim 2 where n is 1.
13. A compound of formula

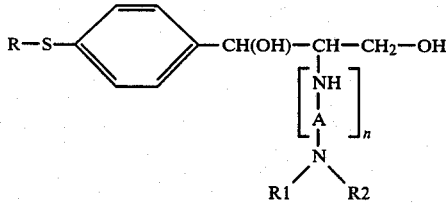

wherein R is an alkyl having from 1 to 4 carbon atoms;
n is 0 or 1;
A is an alkyl having from 2 to 6 carbon atoms;
R1 is hydrogen or an alkyl having from 1 to 6 carbon atoms;
R2 is a phenoxyalkyl, a mono- or diphenylalkyl where the alkyl has from 1 to 6 carbon atoms and the phenyl moiety can be substituted by one or two substituents, equal or different between them, which are selected from the group consisting of halogen, 1-4 C alkyl and 1-4 C alkoxy; or
R1 and R2, together with the nitrogen atom to which they are linked, form a piperozinyl ring which can be substituted on one nitrogen by a 3-6 C cycloalkyl, a 1-6 C alkyl or by a mono- or diphenylalkyl where, in turn, the alkyl has from 1 to 6 carbon atoms and the phenyl moiety can be substituted by one or two substituents, equal or different between them, which are selected from the group consisting of halogen, 1-4 C alkyl and 1-4 C alkoxy, with the proviso that when n is 1 then R2 can be an alkyl having 1 to 6 carbon atoms, and pharmaceutically acceptable salts thereof with organic and inorganic pharmaceutically acceptable acids.

14. A compound according to claim 13, characterized in that

R is methyl or ethyl;
n is 0 or 1;
A is ethyl;
R1 is hydrogen, methyl or ethyl;
R2 is phenoxyalkyl, a mono- or diphenylalkyl where the alkyl has 1-6 C and the phenyl moiety is substituted by one or two substituents, equal or different between them, which are selected from the group consisting of halogen and 1-4 C alkoxy; or
R1 and R2, together with the nitrogen atom to which they are linked, form a piperazinyl radical where the terminal nitrogen is substituted by a cyclohexyl, a diphenylmethyl or a di(fluorophenyl)-methyl with the proviso that when n is 1 then R2 can be an alkyl having 1 to 6 carbon atoms.

15. A pharmaceutical composition comprising a compound of the formula

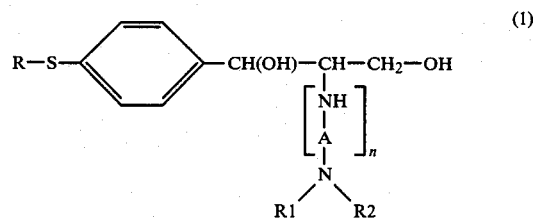

wherein R is an alkyl having from 1 to 4 carbon atoms;
n is 0 or 1;
A is an alkyl having from 2 to 6 carbon atoms;
R1 is hydrogen or an alkyl having from 1 to 6 carbon atoms;
R2 is a phenoxyalkyl, a mono- or diphenylalkyl where the alkyl has from 1 to 6 carbon atoms and the phenyl moiety can be substituted by one or two substituents, equal or different between them, which are selected from the group consisting of halogen, 1-4 C alkyl and 1-4 C alkoxy; or
R1 and R2, together with the nitrogen atom to which they are linked, form a piperazinyl ring which can be substituted on one nitrogen by a 3-6 C cycloalkyl, a 1–6 C alkyl or by a mono- or diphenylalkyl where, in turn, the alkyl has from 1 to 6 carbon atoms and the phenyl moiety can be substituted by one or two substituents, equal or different between them, which are selected from the group consisting of halogen, 1–4 C alkyl and 1–4 C alkoxy, and pharmaceutically acceptable salts thereof with organic and inorganic pharmaceutically acceptable acids in an amount suitable for use as a calcium antagonist, an antiarrhythmic agent together with one or more pharmaceuticl excipients.

16. A pharmaceutical composition according to claim 15 comprising a compound of formula (I)

R is methyl or ethyl;
n is 0 or 1;
A is ethyl;
R1 is hydrogen, methyl or ethyl;
R2 is phenoxyalkyl, a mono- or diphenylalkyl where the alkyl has 1–6 C and the phenyl moiety is substituted by one or two substituents, equal or different between them, which are selected from the group consisting of halogen and 1–4 C alkoxy; or
R1 and R2, together with the nitrogen atom to which they are linked, form a piperazinyl radical where the terminal nitrogen is substituted by a cyclohexyl, a diphenylmethyl or a di(fluorophenyl)-methyl in an amount suitable for use as a calcium antagonist, an antiarrhythmic agent or a vasodilating agent together with one or more pharmaceutical excipients.

17. A method comprising administering to an animal in need of a calcium antagonistic, an antiarrhythmic agent or a vasodilating agent an amount of a compound of the formula

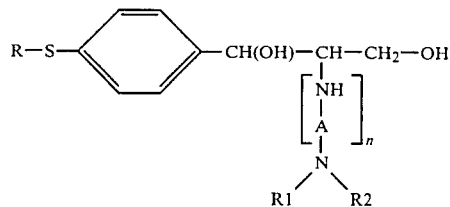

wherein R is an alkyl having from 1 to 4 carbon atoms;
n is 0 or 1;
A is an alkyl having from 2 to 6 carbon atoms;
R1 is hydrogen or an alkyl having from 1 to 6 carbon atoms;
R2 is a phenoxyalkyl, a mono- or diphenylalkyl where the alkyl has from 1 to 6 carbon atoms and the phenyl moiety can be substituted by one or two substituents, equal or different between them, which are selected from the group consisting of halogen, 1–4 C alkyl and 1–4 C alkoxy; or
R1 and R2, together with the nitrogen atom to which they are linked, form a piperozinyl ring which can be substituted on one nitrogen by a 3–6 C cycloalkyl, a 1–6 alkyl or by a mono- or diphenylalkyl where, in turn, the alkyl has from 1 to 6 carbon atoms and the phenyl moiety can be substituted by one or two substituents, equal or different between them, which are selected from the group consisting of halogen, 1–4 C alkyl and 1–4 C alkoxy, and pharmaceutically acceptable salts thereof with organic and inorganic pharmaceutically acceptable acids effective for such purpose.

* * * * *